(12) United States Patent
Carey et al.

(10) Patent No.: US 6,895,811 B2
(45) Date of Patent: May 24, 2005

(54) DETECTION OF SMALL HOLES IN LAMINATES

(75) Inventors: Gregory F. Carey, Plymouth, MA (US); James H. Wyner, Boston, MA (US); Philip J. Prakop, Middleboro, MA (US); A. Michael Nahmias, Wakefield, RI (US)

(73) Assignee: Shawmut Corporation, West Bridgewater, MA (US)

( * ) Notice: Subject to any disclaimer, the term of this patent is extended or adjusted under 35 U.S.C. 154(b) by 66 days.

(21) Appl. No.: 10/022,469

(22) Filed: Dec. 14, 2001

(65) Prior Publication Data

US 2003/0110832 A1 Jun. 19, 2003

(51) Int. Cl.$^7$ .............................. G01M 3/02; G01M 3/20
(52) U.S. Cl. .............................. 73/159; 73/40; 73/37.6; 73/37.7; 73/38
(58) Field of Search ............................. 73/40, 37, 38, 73/37.6, 53.03

(56) References Cited

U.S. PATENT DOCUMENTS

| | | | |
|---|---|---|---|
| 2,310,111 A | * | 2/1943 | Norlander ........................ 436/5 |
| 3,254,526 A | * | 6/1966 | Yarbrough ...................... 73/40 |
| 3,371,518 A | * | 3/1968 | Keyes ............................ 73/38 |
| 3,405,555 A | * | 10/1968 | Wissinger et al. ............ 73/159 |
| 3,646,353 A | * | 2/1972 | Bhullar et al. ......... 250/559.48 |
| 3,675,476 A | * | 7/1972 | Zapfe ....................... 73/150 R |
| 3,811,317 A | * | 5/1974 | Leonard et al. ................. 73/40 |
| 3,908,044 A | * | 9/1975 | Gunning ...................... 427/209 |
| 3,937,064 A | * | 2/1976 | Wolf et al. ...................... 73/40 |
| 3,970,857 A | * | 7/1976 | Buckson ................... 250/559.1 |
| 4,570,074 A | * | 2/1986 | Jette ....................... 250/559.49 |
| 4,577,969 A | * | 3/1986 | Tagaya ........................ 356/394 |
| 4,949,607 A | * | 8/1990 | Yuito ........................... 83/76.7 |
| 4,982,600 A | * | 1/1991 | Kiso et al. ..................... 73/104 |
| 5,049,216 A | * | 9/1991 | Shead et al. ................... 156/64 |
| 5,095,214 A | * | 3/1992 | Eder ....................... 250/559.03 |
| 5,196,799 A | * | 3/1993 | Beard et al. ................. 324/557 |
| 5,274,243 A | * | 12/1993 | Hochgraf ............... 250/559.41 |
| 5,493,899 A | * | 2/1996 | Beck et al. .................. 73/40.7 |
| 5,672,407 A | * | 9/1997 | Beckett ....................... 428/137 |
| 5,847,265 A | * | 12/1998 | Olofson ........................ 73/40 |
| 6,097,427 A | * | 8/2000 | Dey et al. ...................... 348/92 |
| 6,126,898 A | * | 10/2000 | Butler ........................ 420/529 |
| 6,183,599 B1 | * | 2/2001 | Oriaran et al. .............. 162/112 |
| 6,204,669 B1 | * | 3/2001 | Beard et al. ................. 324/557 |
| 6,259,109 B1 | * | 7/2001 | Dalmia et al. .......... 250/559.08 |
| 6,288,554 B1 | | 9/2001 | Yasumoto ................... 324/558 |
| 6,345,453 B1 | * | 2/2002 | Ilomaki et al. ............... 34/508 |
| 6,409,921 B1 | * | 6/2002 | Muller et al. ............... 210/644 |
| 6,410,465 B1 | * | 6/2002 | Lim et al. .................... 442/389 |
| 6,531,707 B1 | * | 3/2003 | Favreau et al. ......... 250/559.46 |
| 6,655,192 B2 | * | 12/2003 | Chavdar ........................ 73/38 |
| 6,818,083 B2 | * | 11/2004 | McAmish et al. .......... 156/73.1 |
| 2002/0019187 A1 | * | 2/2002 | Carroll et al. ............... 442/394 |
| 2002/0109112 A1 | * | 8/2002 | Guha et al. ............ 250/559.46 |
| 2003/0074954 A1 | * | 4/2003 | Engle et al. .................... 73/38 |

FOREIGN PATENT DOCUMENTS

| | | | | |
|---|---|---|---|---|
| EP | 1098191 A1 | | 9/2001 | |
| JP | 61175540 A | * | 8/1986 | ............ G01M/3/12 |
| JP | 63050746 A | * | 3/1988 | .......... G01N/27/20 |
| JP | 06018445 A | * | 1/1994 | .......... G01N/21/89 |
| JP | 06222016 A | * | 8/1994 | .......... G01N/21/89 |
| JP | 07230633 A | * | 8/1995 | ............ G11B/7/26 |

(Continued)

Primary Examiner—Hezron Williams
Assistant Examiner—David A. Rogers
(74) Attorney, Agent, or Firm—Fish & Richardson P.C.

(57) ABSTRACT

Laminates are tested for the presence of small holes. For example, when a laminate is moving through a processing machine in a direction along a length of the laminate, a vacuum is applied to a surface of the laminate and the surface of the laminate is inspected to detect liquid that has penetrated from another surface of the laminate through small holes to the inspected surface.

42 Claims, 4 Drawing Sheets

FOREIGN PATENT DOCUMENTS

| | | | | |
|---|---|---|---|---|
| JP | 08229530 A | * | 9/1996 | ............. B09B/1/00 |
| JP | 11030591 A | * | 2/1999 | .......... G01N/21/89 |
| JP | 2000241357 A | * | 9/2000 | .......... G01N/21/89 |
| JP | 2000288066 A | | 10/2000 | |
| WO | WO 99/54134 | | 10/1999 | |
| WO | WO 00/06377 | | 2/2000 | |

* cited by examiner

DETECTION OF SMALL HOLES IN LAMINATES

TECHNICAL FIELD

This invention relates to detection of small holes in laminates.

BACKGROUND

Composite laminates of textile materials, for example, often include a barrier film to prevent the passage of liquids and gases through the laminate. In addition to the barrier film, these barrier laminates include other layers such as foams, fabrics, nonwovens, and breathable films.

Examples of barrier laminates include waterproof breathable laminates, breathable chemical protection laminates, viral protection laminates, mold-in-place laminates, and allergy proof and fluid proof laminates. Generally these laminates are manufactured by using heat, pressure and/or adhesives to adhere layers of the laminate together.

To function properly as a barrier, these laminates generally must be non-porous, i.e., free of even small holes. For example, to form a fabric-covered seat cushion, a barrier laminate may be vacuum drawn into a female tool, e.g., at a vacuum of about 15–25 inches of water, and a foaming liquid applied to the exposed surface of the laminate. In this case, a large pressure differential is applied to the laminate, and as a result the foaming liquid may penetrate even very tiny holes, potentially resulting in an unacceptable product. Similarly, in low pressure injection molding, a barrier laminate may be laid into a mold and a thermoplastic injected into the mold at a pressure that forces the laminate against the mold surface. In this case, the positive pressure exerted by the plastic may force plastic through even tiny holes in the laminate.

A variety of tests have been used to check laminates for small holes. Generally, testing is performed off-line on samples of the laminate. In some off-line tests a liquid is applied to one side of the sample and a vacuum is drawn on the opposite side. Because testing is performed off-line, there is typically a time-lag between production and testing, which may result in large quantities of defective laminate being manufactured before a problem is identified.

SUMMARY

The invention features methods of testing laminates for the presence of small holes. By small holes, we mean holes having a diameter that is sufficiently small so that the surface tension of the liquid that is being applied to the web for testing will not permit the liquid to pass through them under normal ambient conditions. In the case of water, such small holes have an average diameter of less than about 700 $\mu$m. By pinholes, we mean holes having an average diameter of less than about 30 $\mu$m. Some pinholes may have diameters of less than about 15 $\mu$m, some have diameters of less than about 2 $\mu$m.

In general, in one aspect, the invention features a method that includes moving a web that includes a film through a machine in a direction along a length of the web, causing a liquid to pass from one surface of the web through small holes to another surface of the web by applying a vacuum to a surface of the web, and making the web available for inspecting of one of the surfaces of the web to detect liquid that has passed from another surface of the web through the small holes at the inspection surface, at least one of the causing and inspecting steps occurring while the web is moving through the machine.

Some implementations include one or more of the following features. The web includes a laminate of the film with another material. The inspecting is done while the web is moving through the machine. Alternatively, the inspecting is done after the web is removed from the machine. The liquid is applied to the other surface from a supply of liquid. The liquid is applied to the other surface while the web is moving. The liquid is applied, the vacuum is applied, and the inspection are all done while the web is moving. The liquid forms a film on the other surface. The liquid is applied in a film that substantially spans a full width of the surface. The liquid is applied to the other surface from a dispenser that spans the width of the web.

The liquid contains a colorant. The liquid stains the inspected surface and the inspecting includes observing the stains. After inspection, the inspected surface of the web is rinsed to reduce staining resulting from the liquid penetrating the web.

The small holes include pinholes. The vacuum produces a pressure differential between the one surface and the other surface that is at least as large as a maximum pressure differential between the surfaces that is expected to occur during subsequent processing and use, e.g., at least 15% larger than the maximum expected pressure differential. The vacuum is formed using a nozzle that spans the width of the web. The applying of the vacuum and the applying of the liquid are performed substantially simultaneously The other surface is an exposed outer surface of the web. The one surface and the other surface are disposed on opposite sides of the film layer of the laminate. The laminate includes a long web of fabric. The laminate is formed in the machine. The web is moving through the machine at a speed of at least 10 ft/min. The laminate includes a barrier film and one or more porous layers. The porous layer(s) are selected from the group consisting of fabrics, non-wovens, foams, and breathable sheet materials.

The inspecting step includes observing the inspected surface using a machine vision device. Alternatively, inspection includes visual inspection by a human. The method also includes triggering an alarm upon detection of liquid, and/or flagging a portion of the web adjacent the location at which the liquid is detected. The inspecting and the applying of the vacuum are performed substantially simultaneously.

The method further includes, after inspection, removing residual liquid from the first surface of the web. The method further includes collecting any liquid that is drawn through the web and/or any liquid that is used to rinse the web, and reusing it.

In a further aspect, the invention features a method including (a) moving a long web of laminate through a machine in a direction along a length of the laminate, and (b) while the laminate is moving through the machine, (i) applying a vacuum to an exposed inspection surface of the laminate from a vacuum source that spans a width of the laminate, (ii) supplying liquid to a second, exposed surface of the laminate from a source that spans a width of the laminate to form a film of liquid, and (iii) inspecting the surface of the laminate using machine vision to detect liquid that has passed from the other surface of the laminate through small holes to the inspected surface. In this method, the vacuum produces a pressure differential between the one surface and the other surface that is at least as large as a maximum pressure differential between the surfaces that is expected to occur during subsequent processing and use, and the one surface and the other surface are disposed on opposite sides of a barrier layer of the laminate.

In another aspect, the invention features a method including moving a laminate through a machine, and while the laminate is moving, automatically inspecting an inspection surface of the laminate for stains caused by liquid having penetrated pinholes in the laminate.

In yet another aspect, the invention features an apparatus including an applicator configured to dispense liquid onto a first surface; a vacuum port positioned to apply a vacuum to a second surface below the first surface; and, downstream from the applicator and the vacuum port, a vision system aimed at the second surface and configured to detect liquid at the second surface.

Implementations may include one or more of the following features. The apparatus further includes a rotary vacuum roll in communication with the vacuum port. The apparatus further includes, downstream from the vacuum port, a scraper configured to remove liquid from the first surface. The apparatus further includes, downstream from the vacuum port, a rinse applicator configured to dispense liquid onto a location on the second surface. The applicator is configured to dispense said liquid in a film that is substantially continuous across the first surface. The apparatus further includes a driver that is configured to move a sheet material between the applicator and the vacuum port at a speed of at least 10 ft/min.

The invention also features a method including moving a web that includes a film through a machine, and, while the web is moving, automatically inspecting an inspection surface of the web for stains caused by liquid having penetrated pinholes in the web.

In some implementations, the web is a laminate, and the laminate is inspected in-line with the laminating equipment. This allows manufacturing problems that cause small holes in the laminate to be detected immediately and corrected quickly. As a result, waste laminated material can be minimized, and defective laminate can be removed from processing prior to its incorporation into value-added products. Thus, for example, $10 worth of laminate can be scrapped, rather than a $100 part manufactured with the laminate. Inspection can also be performed quickly, and with minimal added processing time.

Other features and advantages of the invention will be apparent from the description and drawings, and from the claims.

DETAILED DESCRIPTION

Figure 1:
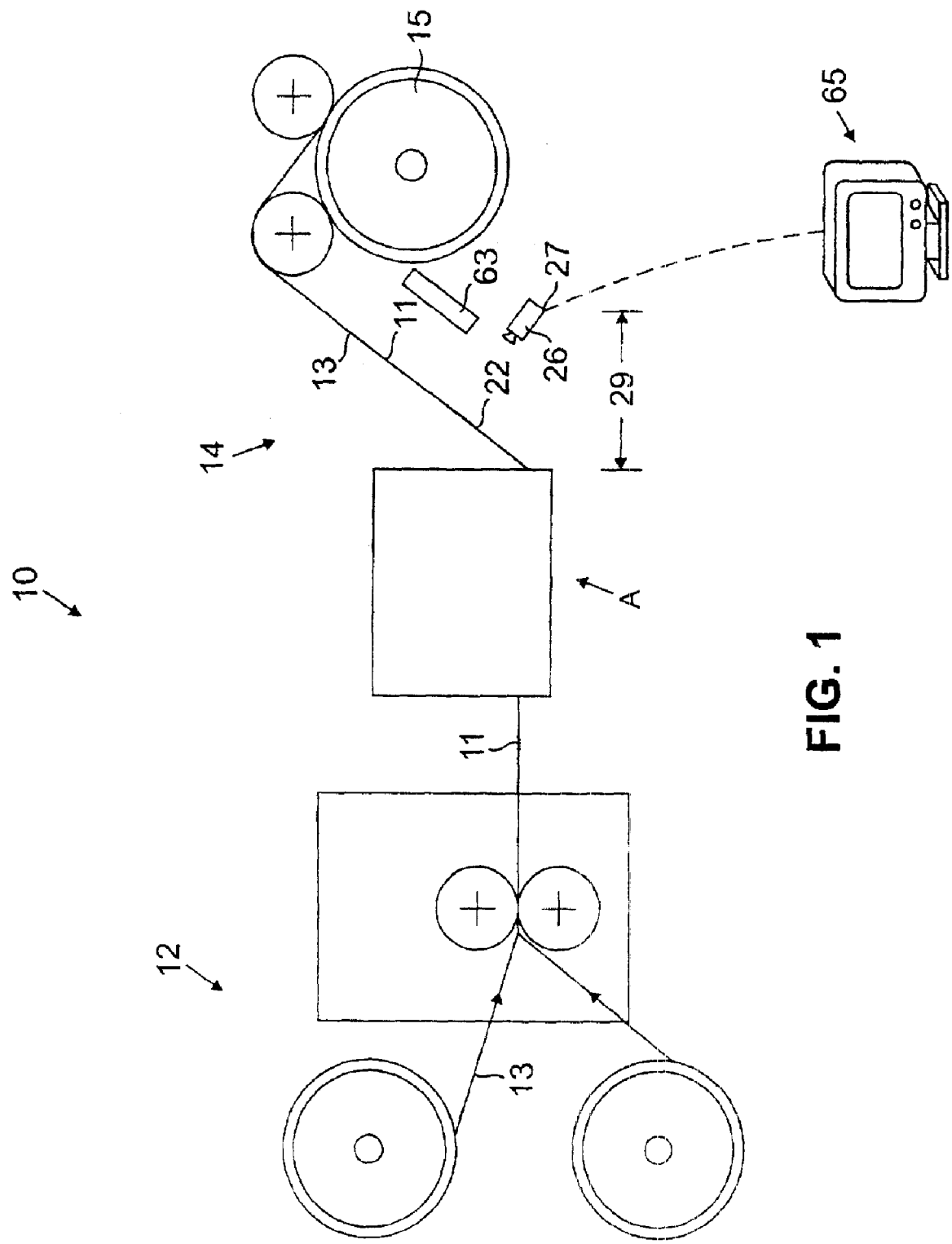
FIG. 1 is a schematic diagram of a production line.

Referring to FIG. 1, a production line 10 includes a lamination area 12, and a testing area 14. A long web of a laminate 11 is formed from layers of sheet material in lamination area 12, the layers of sheet material including at least one layer 13 configured to provide barrier properties to the laminate. Laminate 11 may include, for example, (a) a layer of fabric, e.g., tricot, and/or nonwoven, (b) a layer of foam and/or a breathable film, and (c) a layer of a barrier film. The laminate may be formed by any suitable process, e.g., flame lamination, adhesive, or applying heat and pressure at a nip. Adhesive may be applied, for example, as a hot melt or by solvent coating. Suitable adhesives include urethanes, olefins, polyesters, polyamides, PVC, PVDC, nitrocellulose and butyrates. Laminate 11 may be used in a wide variety of applications, including waterproof breathable laminates, breathable chemical protection laminates, viral protection laminates, and allergy proof and fluid proof laminates.

The laminate 11 then travels to testing area 14, where it is tested for the effectiveness of its barrier properties, i.e., tested for the presence of small holes such as pinholes, as the laminate is moving along the production line and passes through the testing area 14. As it exits testing area 14, the laminate is wound up on a take-up roll 15. If desired, the laminate may be subjected to further inspection, testing or processing before or after it is wound up on take-up roll 15. The laminate may be drawn through the production line at relatively low speeds, e.g., 10 ft/min, or relatively high speeds, e.g., up to 400 ft/min or more.

Figure 1A:
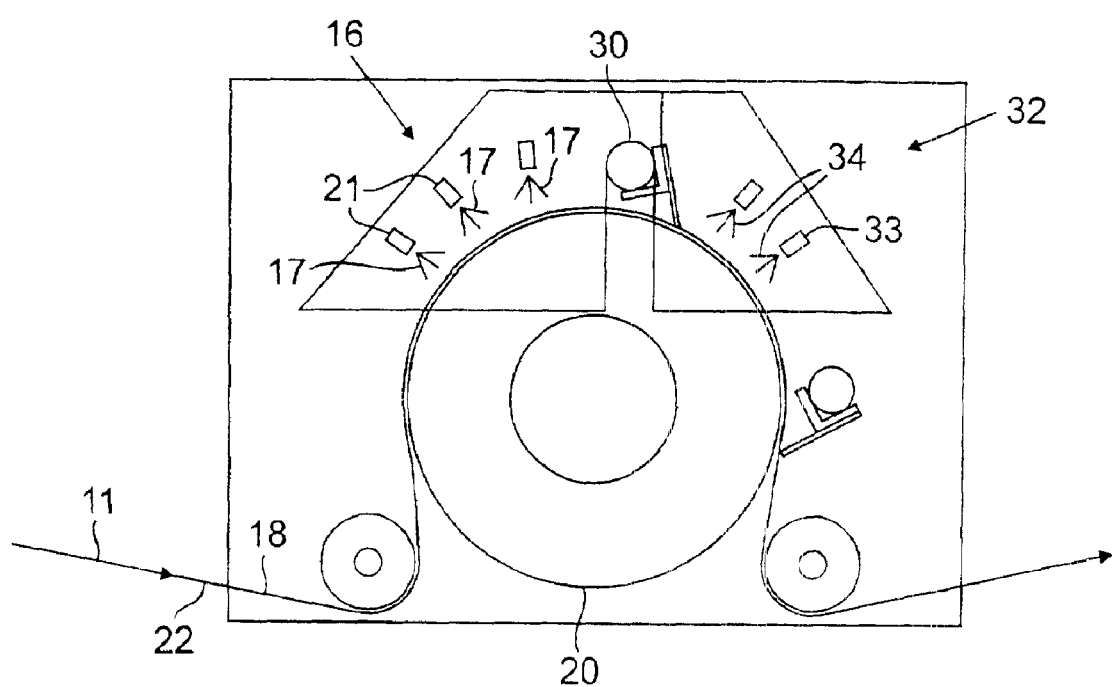
FIG. 1A is a more detailed schematic diagram of area A of FIG. 1.
Figure 1B:
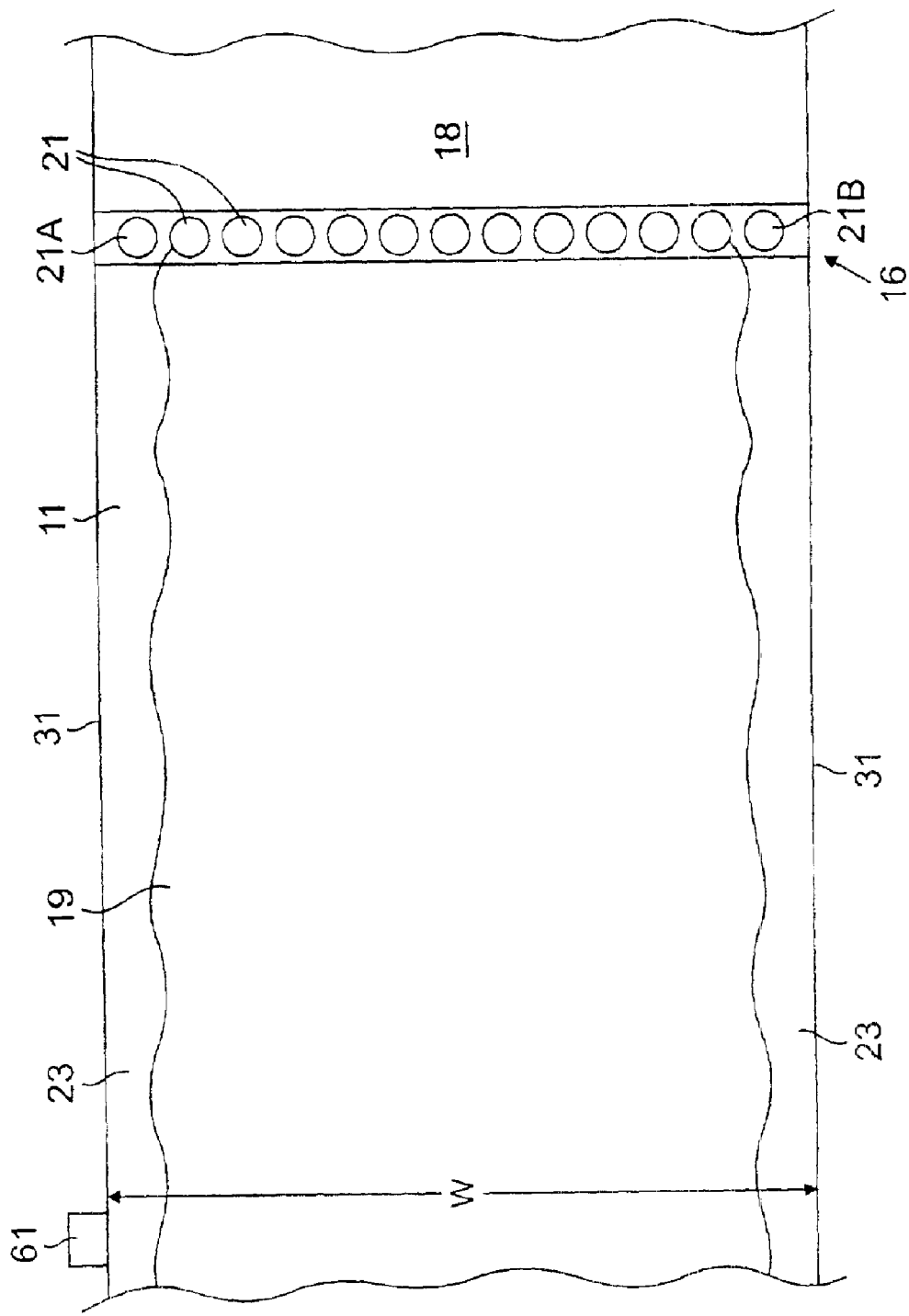
FIG. 1B is a top view of a laminate as it passes through area A.

Referring to FIG. 1A, testing area 14 includes an applicator 16, configured to apply a volume of liquid 17 to surface 18 of the laminate 11. Suitable applicators include spray nozzle systems, for example spray nozzles 21 as shown in FIGS. 1A and 1B. Other suitable applicators include roll coating systems and felt applicators (not shown). Suitable liquids generally have low viscosity and low surface tension. Suitable liquids include water; alcohols, e.g., methyl, ethyl, or isopropyl alcohol; alcohol/water solutions; and other hydrocarbon solvents, e.g., acetates, alone or in solution with water. Surfactants may be added, to reduce surface tension, provided the surfactant does not have a deleterious effect on the laminate. The liquid may include a colorant, e.g., a dye, for reasons that will be described below. One specific example of a liquid that is useful when testing for pinholes in a flame-laminated laminate made of polyester fabric, a urethane foam core, and a thermoplastic urethane barrier film consists of 30–70% isopropyl alcohol in water, colored with food coloring.

As shown in FIG. 1B, the liquid 17 is applied in a continuous film 19 that substantially spans the full width W of the laminate (the cross-machine dimension). Any desired volume of liquid may be applied, as long as the width of the laminate that needs to be tested is covered. By substantially spans we mean that the film 19 covers as much of the width as will be used in a finished product, typically within a margin of 1–2 inches of each longitudinal edge 31 of the laminate. The 1–2 inch margin (e.g., margin 23 in FIG. 1B) would generally be discarded and therefore need not be tested. These liquid-free margins 23 along the edges 31 of the laminate can be provided, for example, by applying the liquid 17 from a number of closely spaced nozzles 21, and turning off the nozzles that are adjacent the edges of the laminate (nozzles 21A and 21B in FIG. 1B). If desired, the entire width of the laminate may be covered with liquid. In this case, it may be desirable to provide a barrier to prevent liquid from flowing over the edges of the laminate.

As shown in FIG. 1A, testing area 14 also includes a vacuum source 20, positioned below the applicator 16. The vacuum source may be positioned immediately below the applicator 16, as shown, or downstream of the applicator by a distance that allows time for the applied liquid to thoroughly coat the upper surface of the laminate, e.g., an inch or less downstream. The vacuum source faces the opposite surface 22 of the laminate from below. Vacuum source 20 is in communication with a vacuum device that is configured to apply to the laminate a pressure differential between the two surfaces 18, 22. Suitable vacuum devices include a vacuum bar, conveyor or table perforated with a hole pattern, a vacuum slot, or a rotary vacuum roll. The vacuum device should generally be configured so as not to damage the surface 22 of the laminate.

The pressure differential may be at least as large as the maximum pressure differential that is expected to occur between the two surfaces during subsequent processing and use. This will simulate use conditions, and allow detection of pinholes of a size that will cause leakage during expected use conditions. Preferably, the pressure differential is at least 15% larger, more preferably at least 20% larger than the maximum expected pressure differential.

Figure 2:
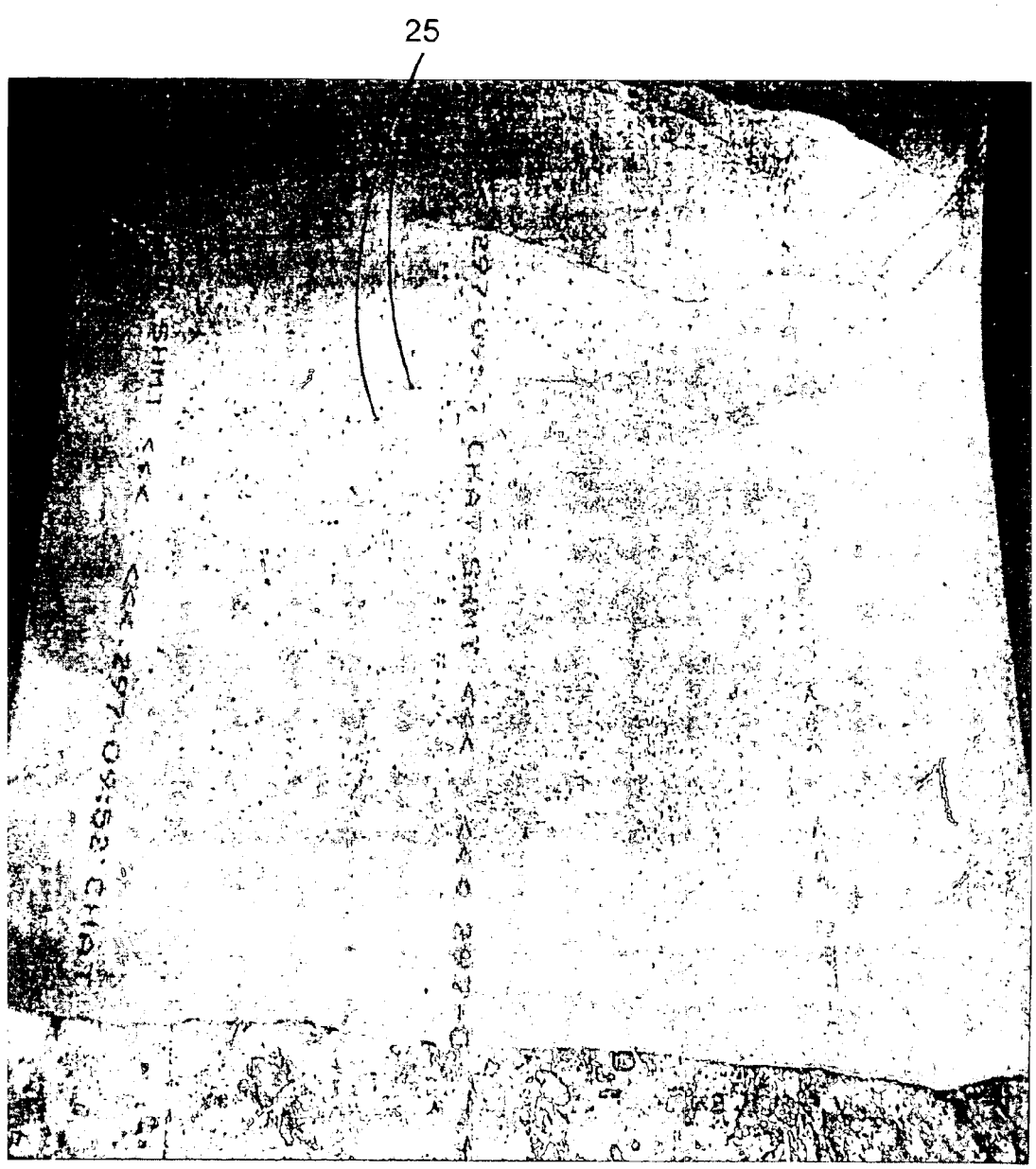
FIG. 2 is a photograph of a surface of a laminate after penetration of a colorant-containing liquid.

The pressure differential applied to the laminate overcomes the surface tension of the liquid which would otherwise tend to prevent it from entering the pin holes (e.g., by capillary action) and being drawn to the lower surface of the laminate. If there are any small holes in the laminate the pressure differential causes the liquid to be drawn through the small holes to surface 22. When the liquid reaches surface 22 it will tend to stain the surface in the vicinity of the holes. FIG. 2 shows a photograph of the stained surface after the liquid has been drawn through the small holes 25. If the liquid contains a colorant, the colored liquid will stain the surface 22 in a way that is even more apparent than without the colorant.

Suitable pressure differentials will depend on the maximum expected pressure differential for a particular application, but are generally in the range of 10 to 50 inches of water, typically 15 to 30 inches of water. Higher pressure differentials may allow the laminate to be passed more quickly through testing area 14. Higher pressure differentials also may allow higher surface tension liquids to be used, if desired.

As shown in FIG. 1, at a location 27 that is sufficiently downstream from the vacuum port to give time for the liquid to be drawn through the small holes to the bottom surface is an inspection station 26. The distance 29 between the location of the vacuum port and the location of the inspection station may be very small, for example an inch or less, but for convenience may be 6 feet or more. At inspection station 26, the surface 22 of the laminate is inspected to detect liquid that has passed from surface 18 through to surface 22. Inspection may be performed by a machine vision system or other automated inspection system, or by human visual inspection. Suitable machine vision systems are commercially available, e.g., from Elba, and Cognex Systems. If a colorant is used, the surface 22 may be inspected for staining. If no colorant is used, the surface 22 may be visually inspected for wetness, or may be otherwise tested for surface moisture.

The presence of pinholes may indicate that the barrier film that is being fed to the lamination area 12 should be inspected and tested for pinholes. It may be possible to make these adjustments without stopping the process, or it may be necessary to bring the production line down until the problem is corrected. When production begins again, the operator can easily determine whether the problem has been successfully been corrected based on the results at inspection station 26.

If staining or moisture is detected, an alarm may be triggered by the machine vision system, and/or a flag 61 (FIG. 1B) may be placed on an edge of the laminate near the location of the staining/moisture. The flag may be applied at a marking station 63. To preserve the continuity of the process, the portion of the laminate containing the hole(s) will generally be wound up on the take-up roll 15, and the portion removed and discarded during subsequent manufacturing steps. When more that a few pinholes are detected, this may indicate to the operator of the machine that the process parameters should be adjusted to address the problem causing the holes.

The machine vision system can be arranged to display to the operator on a monitor 65 information about the number of pinholes that have been detected in a particular recent section of the laminate web, or statistical information about the history of pinholes over a longer section of the web. The statistical information could indicate one or more portions of the web, in a cross-wise direction, that have experienced more or less than average pinholes, or the variations of patterns of pinholes along the length of the web. The machine vision system might also be arranged to display to the user images of portions of the laminate or maps that represent the surface of the laminate and show the actual locations of pinholes or the average locations of pinholes in the laminate. These features allow the operator to immediately observe if a process parameter is moving out of control, based on the number of pinholes being detected by the vision system. As a result, corrective action can be taken immediately, minimizing the amount of defective laminate that is produced.

The machine vision system also frees the operator from standing continually at an inspection station. The machine vision system can be configured to provide an audible alarm and/or a visual indicator (e.g., a flashing light) when pinholes are detected, so that the operator may step away from the monitor 65 and still be notified when pinholes occur. Moreover, the machine vision system can be configured to store pinhole data and images of the web surface. Thus, if the operator does not see a pinhole before the laminate is rolled onto the take-up roll, the operator can later pull up a picture of the pinhole on the monitor, and print the picture if desired.

Additionally, the machine vision system can be configured to document the number and location of pinholes over an entire run of material, allowing the manufacturer to provide a quality record to a purchaser of the laminate. The machine vision system can also be configured to track the number of pinholes by shift, by operator, by product type and by process condition. This information can be used to develop a better understanding of the lamination process and to optimize the process, allowing pinholes to be more easily avoided and corrected and improving product quality.

As shown in FIG. 1A, if desired, the production line may also include a scraper 30, configured to remove excess liquid 17 from surface 18 of the web after the vacuum has been applied. If a colorant is used in the liquid 17, the production line may also include a rinse station 32, where a rinsing liquid 34 is applied from nozzles 33 to surface 18 to remove or reduce the staining produced by the colored liquid.

Other embodiments are within the scope of the following claims.

For example, while the invention has been described above in the context of laminates, the methods described are also suitable for use in testing other types of webs, e.g., barrier films that are not laminated to other layers. In some cases, it may be desirable to cover the rotary vacuum described above with a thin layer of foam to prevent damage to the film and enhance wetting of the inspection surface of the film with any fluid that passes through the film. If a colorant is included, the colorant may be selected to effectively wet the inspection surface of the film.

Additionally, while in the implementation described above inspection takes place online, in some applications the inspection station may be omitted. Inspection can be performed in a later, post-production step, or omitted entirely. For example, the finished laminate may be shipped to a customer without inspection, and the customer may inspect the inspection surface for staining. The customer may then remove any stained areas (areas with holes) if desired.

What is claimed is:

1. A method comprising
   moving a web comprising a film through a machine in a direction along a length of the web,
   causing a liquid to pass from a first surface of the web through small holes to a second surface of the web by applying a vacuum to the second surface of the web, and
   inspecting the second surface of the web to detect liquid that has passed from the first surface of the web through the small holes at the inspection surface,
   at least one of the causing and inspecting steps occurring while the web is moving through the machine.

2. The method of claim 1 wherein the web comprises a laminate of the film with another material.

3. The method of claim 2 in which the first surface and the second surface are disposed to opposite sides of the film layer of the laminate.

4. The method of claim 2 in which the laminate comprises a long web of fabric.

5. The method of claim 2 wherein the laminate is formed in the machine.

6. The method of claim 2 wherein the laminate comprises a barrier film and one or more porous layers.

7. The method of claim 6 wherein the porous layer(s) are selected from the group consisting of fabrics, non-wovens, foams, and breathable sheet materials.

8. The method of claim 1 wherein the inspecting is done while the web is moving through the machine.

9. The method of claim 1 wherein the inspecting is done after the web is removed from the machine.

10. The method of claim 1 in which the liquid is applied to the first surface from a supply of liquid.

11. The method of claim 10 wherein the applying of the vacuum and the applying of the liquid are performed substantially simultaneously.

12. The method of claim 10 wherein the applying of the liquid and the inspecting are performed substantially simultaneously.

13. The method of claim 1 in which the liquid is applied to the first surface while the web is moving.

14. The method claim 13 in which the liquid is applied, the vacuum is applied, and the inspection is done while the web is moving.

15. The method of claim 1 in which the liquid is applied to the first surface while the web is moving from a supply end to a take up end of the machine.

16. The method of claim 1 in which the liquid forms a film on the first surface.

17. The method of claim 16 in which the liquid is applied in a film that substantially spans a full width of the first surface.

18. The method of claim 1 wherein the liquid contains a colorant.

19. The method of claim 18 wherein the method further comprises, after inspection, rinsing the second surface of the web to reduce staining of the surface.

20. The method of claim 19 further comprising collecting liquid used to rinse the web and reusing it.

21. The method of claim 19 wherein said rinsing liquid comprises an alcohol solution.

22. The method of claim 21 wherein said alcohol solution includes water.

23. The method of claim 1 wherein the small holes comprise pinholes.

24. The method of claim 1 wherein the vacuum produces a pressure differential between the first surface and the second surface that is at least as large as a maximum pressure differential between the surfaces that is expected to occur during subsequent processing and use.

25. The method of claim 24 wherein the pressure differential is at least 15% larger than the maximum expected pressure differential.

26. The method of claim 1 in which the second surface is an exposed outer surface of the web.

27. The method of claim 1 in which the inspecting comprises using a machine vision device.

28. The method of claim 1 also including triggering an alarm upon detection of liquid.

29. The method of claim 1 in which the liquid stains the inspected surface and the inspecting includes observing the stains.

30. The method of claim 1 in which the liquid is applied to the first surface from a dispenser that spans the width of the web.

31. The method of claim 1 in which the vacuum is formed using a nozzle that spans the width of the web.

32. The method of claim 1 in which the liquid comprises water.

33. The method of claim 32 in which the liquid further comprises a surfactant.

34. The method of claim 1 in which the liquid comprises alcohol.

35. The method of claim 1 wherein the inspecting and the applying of the vacuum are performed substantially simultaneously.

36. The method of claim 1 further comprising, if liquid is detected on the inspected surface, flagging a portion of the web adjacent the location at which the liquid is detected.

37. The method of claim 1 wherein inspection comprises visual inspection by a human.

38. The method of claim 1 wherein the web is moving through the machine at a speed of at least 10 ft/mm.

39. The method of claim 1 further comprising, after inspection, removing residual liquid from the first surface of the web.

40. The method of claim 1 further comprising collecting any liquid that is drawn through the web and reusing it.

41. The method of claim 1 wherein inspection includes looking for stains on the second surface.

42. The method of claim 1 in which the liquid comprises a hydrocarbon solvent.

* * * * *